United States Patent

Hosseini et al.

[11] Patent Number: 5,540,860
[45] Date of Patent: Jul. 30, 1996

[54] PROCESS FOR PREPARING COPPER PYRITHIONE

[75] Inventors: Saeed M. Hosseini, Fairport; Charles W. Kaufman, Rochester, both of N.Y.; Patrick Hobbs, Howth, Ireland; John J. Jardas, Rochester, N.Y.; Murray A. Ruggiero, East Haven; Shoaib Arif, Cheshire, both of Conn.

[73] Assignee: Olin Corporation, Cheshire, Conn.

[21] Appl. No.: 203,207

[22] Filed: Feb. 28, 1994

[51] Int. Cl.⁶ .............................. A01N 5/02; B01J 13/00; C07F 1/08
[52] U.S. Cl. .................. 252/308; 252/311; 252/314; 252/363.5; 514/188; 514/937; 546/2; 546/6
[58] Field of Search .................................. 252/311, 314, 252/363.5, 308; 514/188, 937; 546/2

[56] References Cited

U.S. PATENT DOCUMENTS

| | | |
|---|---|---|
| 2,809,971 | 10/1957 | Bernstein et al. |
| 3,785,985 | 1/1974 | Grand ........................ 252/106 |
| 4,323,683 | 4/1982 | Bolich, Jr. et al. ............... 546/6 |
| 4,345,080 | 8/1982 | Bolich, Jr. ...................... 546/6 |
| 4,835,149 | 5/1989 | Burke et al. ................. 514/188 |
| 5,057,153 | 10/1991 | Ruggiero ................. 514/188 X |
| 5,185,033 | 2/1993 | Hani et al. ............... 514/188 X |
| 5,238,490 | 8/1993 | Farmer, Jr. et al. ........ 514/188 X |
| 5,246,489 | 9/1993 | Farmer, Jr. et al. .......... 106/18.33 |

*Primary Examiner*—Richard D. Lovering
*Attorney, Agent, or Firm*—Dale L. Carlson

[57] ABSTRACT

The present invention relates to a process for producing a gel-free dispersion or solution of copper pyrithione employing at least one surfactant. Also claimed is the dispersion or solution itself, as well as a solid particulate copper pyrithione composition comprising copper pyrithione particles having a particle shape selected from the group consisting of rods, spheres, needles, platelets and combinations thereof, and optionally containing at least a trace amount of a surfactant on the outer surface of at least a portion of said particles.

6 Claims, No Drawings

PROCESS FOR PREPARING COPPER PYRITHIONE

FIELD OF THE INVENTION

The present invention relates generally to a process for preparing copper pyrithione and, more specifically, to a process for preparing a gel-free dispersion of copper pyrithione using surfactants.

BACKGROUND OF THE INVENTION

Pyrithione salts are well-known salts useful in a wide variety of applications. Heavy metal salts of pyrithione, including zinc, tin, cadmium and zirconium, as well as the magnesium and aluminum salts, in the form of flat platelets suitable for use in shampoo, are disclosed in U.S. Pat. Nos. 4,345,080 and 4,323,683. For example, paints containing a pyrithione salt (e.g. zinc or sodium pyrithione) plus a copper salt (e.g. cuprous oxide or cuprous thiocyanate) are known in the art, as disclosed, for example, in U.S. Pat. No. 5,057,153. U.S. Pat. No. 5,185,033 describes a process for making a paint or paint base containing copper pyrithione or pyrithione disulfide plus cuprous oxide, wherein the paint exhibits stability against gelation during storage. U.S. Pat. No. 5,246,489 discloses a process for providing in situ generation of copper pyrithione in a paint or paint base which comprises incorporating a metal salt of pyrithione, cuprous oxide and a controlled amount of water into the paint either during or after the formation of the paint.

Copper pyrithione itself is now being considered for use in supplementing or supplementing or supplanting zinc pyrithione in view of the fact that copper pyrithione is more favored from a low-toxicity standpoint and provides stability against gellation in products such as paint during storage prior to use. However, seemingly straight-forward processes for producing copper pyrithione, such as by contacting an aqueous solution of any water soluble copper salt with an aqueous solution of sodium pyrithione, have now been found to provide a gelled precipitate of copper pyrithione. The gelled precipitate exhibits poor flowability characteristics, causing processing problems such as flowability and filterability difficulties for the gelled copper pyrithione.

New processes for producing copper pyrithione while avoiding this gellation or thickening problem during production of the copper pyrithione solution or dispersion, would be highly desired by the biocides manufacturing community. The present invention provides are such solution.

SUMMARY OF THE INVENTION

In one aspect, the present invention relates to a process for producing a solution or dispersion of gel-free copper pyrithione which comprises reacting, in an ion-exchange reaction, a reaction mixture comprising a copper salt, a pyrithione salt, and said carrier, to produce said solution or dispersion, said reaction being carried out in the presence of a stabilizing effective amount of at least one surfactant (preferably at least two surfactants), the total amount of said surfactant being sufficient to prevent or inhibit the formation of gels or thick thixotropic precipitate in said carrier.

In another aspect, the present invention relates to a gel-free product produced by a process comprising reacting, in an ion-exchange reaction, a reaction mixture comprising a copper salt, a pyrithione salt, and said carrier, to produce said solution or dispersion, said reaction being carried out in the presence of a stabilizing effective amount of at east one surfactant (preferably at least two surfactants), the total amount of said surfactant being sufficient to prevent or inhibit the formation of gels in said carrier.

In yet another aspect, the present invention relates to a process for producing a gel-free dispersion or solution of copper pyrithione employing at least one surfactant. Also claimed is the dispersion or solution itself, as well as a solid particulate copper pyrithione composition comprising copper pyrithione particles having a particle shape selected from the group consisting of rods, spheres, needles, platelets and combinations thereof, and optionally containing at least a trace amount of a surfactant on the outer surface of at least a portion of said particles.

These and other aspects will become apparent upon reading the following detailed description of the invention.

DETAILED DESCRIPTION OF THE INVENTION

It has now been surprisingly found, in accordance with the present invention, that a solution is provided to a problem that occurs when carrying out an ion-exchange reaction of a copper salt with a pyrithione salt in water or an organic carrier in order to produce copper pyrithione, namely the problem of the formation of a gelatinous copper pyrithione product. The present inventors have solved this problem utilizing surfactant(s) to provide gel-free copper pyrithione in the carrier.

Without wishing to be bound by any particular theory, the efficacy of the surfactant(s) employed in the process of the present invention, in overcoming or avoiding the above-described gellation or thickening problem, is believed by the present inventors to be attributable to the chemical affinity between the copper pyrithione molecule (a polar molecule) and the molecules of surfactant. It is believed that this affinity reduces or eliminates the propensity of the copper pyrithione molecules to hydrogen-bond to each other, thereby reducing or eliminating agglomeration of the copper pyrithione molecules in the form of human eye-visible gelatinous bodies, or agglomerates in the carrier medium (therein after referred to as "gels").

In accordance with the process of the present invention, a reaction is carried out between a copper salt and a pyrithione salt, in an aqueous or organic carrier medium, in the presence of a surfactant. Suitable pyrithione salts are those which are soluble in the organic or aqueous carrier, such as, for example, the alkali metal or alkaline earth metals, such as sodium, calcium, potassium, and magnesium salts of pyrithione, pyrithione acid, or the non-metal salts such as the ethanolamine salt, chitosan salt, and the disulfide salt of pyrithione (which is commercially available as OMADINE MDS). The pyrithione salt is preferably employed in an amount of between about one and about 40 (more preferably between 5 and 25, most preferably between 15 and 25) weight percent, based upon the weight of the reaction mixture.

The copper salt is suitably any salt containing copper that is soluble in the carrier employed in the reaction. For example, if water is the carrier, useful copper salts include copper chloride dihydrate, copper sulfate, copper carbonate, copper nitrate, and copper acetate, as well as combinations thereof. The copper salt is preferably employed in an amount of between about one and about 50 (preferably between 5 and 30, more preferably between 15 and 20) weight percent, based upon the weight of the reaction mixture.

Useful carriers include water, organic solvents, and combinations thereof. Useful organic solvents include alcohols, such as methanol, ethanol, amines such as diethanolamine, ether, esters, and the like.

The surfactant(s) employed in the process of the present invention are suitably selected from the classes of surfactants known as nonionics, anionics, cationics, and amphoterics (the latter being also commonly referred to as "zwitterionics"). The surfactants are suitably employed singly, or in combinations of two, three, or even four surfactants selected from the above-mentioned four classes of surfactants. When use singly, nonionics are preferred, although the anionic surfactants were also found to provide good results. Although less preferred when employed as the sole surfactant, the cationics and amphoteric surfactants provided an improvement in reducing the extent of the gelation problem during production of the copper, as compared to copper pyrithione prepared without employing any surfactant.

Useful nonionic surfactants include linear alcohol alkoxylates, such as the linear alcohol ethoxylates, ethyoxylated/propoxylated block copolymers, ethyoxylated/propoxylated fatty alcohols, and polyoxyethylene cetyl ethers, and the like. Useful linear alcohol alkoxylates are commercially available, for example, under the registered trademark POLY-TERGENT SL-42, a product of Olin Corporation. If desired, the alcohol alkoxylate is suitably end-capped with a lower alkyl group, and such a product is commercially available as POLY-TERGENT SLF-18, a propylene oxide-capped linear alcohol alkoxylate that is also a product of Olin Corporation, and these end-capped linear alcohol alkoxylates are notably low foaming during use. Also advantageous for use in accordance with the present invention are surfactants within the group commercially available as POLY-TERGENT SLF-18B series surfactants, which are surfactants characterized by enhanced biodegradability (also products of Olin Corporation), being alkene oxide-capped linear alcohol alkoxylates, containing ethylene oxide moieties in the backbone, and suitably also containing at least one propylene oxide moiety in the backbone, as disclosed, for example, in U.S. Pat. Nos. 4,925,587 and 4,898,621.

Other useful nonionic surfactants include one commercially available as NEODOL 91-6, a trademarked surfactant product of Shell Chemical. This surfactant is a detergent range mixture of C9–C11 linear primary alcohol ethoxylates having an average of six moles of ethylene oxide per mole of alcohol. Other useful nonionic surfactants include those containing a linear C9–C11 carbon chain and five or six ethylene oxide or propylene oxide groups per molecule.

Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, and alkyl sulfonates. Particularly useful anionics are the alkylated diphenyl oxide sulfonates, and their methods of preparation are well-known, as illustrated by the disclosures of U.S. Pat. Nos. 3,264,242; 3,634,272; and 3,945,437, the disclosures of which are all incorporated herein by reference. Commercial methods of preparation of the alkylated diphenyl oxide sulfonates generally do not produce species which are monoalkylated, monosulfonated, dialkylated or disulfonated. The commercially available species typically are predominately (greater than 90 percent) disulfonated and are a mixture of mono- and di-alkylated with the percentage of dialkylation being about 15 to about 25 percent, and the percentage of monoalkylation being about 75 to 85 percent. Most typically, the commercially available species are about 80 percent monoalkylated and 20 percent dialkylated.

Two illustrative commercially available solutions containing alkylated diphenyl oxide sulfonate surfactants are DOWFAX 8390 and DOWFAX 8390A surfactants, trademarked products of The Dow Chemical Company. In each, the alkyl group is predominantly a hexadecyl C-16 group. These products are suitably employed in a solution fully or partially neutralized with ammonium hydroxide if desired.

An advantageous anionic surfactant is also provided by reacting the above-described alkylated diphenyl oxide sulfonates with a piperazine compound to produce a molar ratio of sulfonate compound to piperazine compound of between about 10:1 and about 1:10, preferably between about 2:1 and about 1:2. Although any piperazine compound can be used for such reaction, preferred compounds include those selected from the group consisting of 1,2-aminoethyl piperazine, 1,4-piperazinediethane sulfonic acid, anhydrous piperazine, hydrated piperazine, and combinations thereof.

Other useful anionics are polycarboxylated alcohol alkoxylates, preferably those selected from the group consisting of the acids or organic or inorganic salts of the following: polycarboxylated linear alcohol alkoxylates, polycarboxylated branched alcohol alkoxylates, polycarboxylated cyclic alcohol alkoxylates, and combinations thereof. These polycarboxylated alcohol alkoxylates typically contain at least two succinic acid radicals per molecule. Preferred polycarboxylated alcohol alkoxylates are those having a backbone containing both poly(propylene oxide) and poly(ethylene oxide) blocks, and such preferred polycarboxylated alcohol alkoxylates are readily commercially available, for example, as POLY-TERGENT CS-1, a trademarked surfactant of Olin Corporation. If desired, at least a portion of the acid groups on the polycarboxylated alcohol alkoxylate are neutralized with a base to provide the corresponding salt. Suitable bases include alkali metal hydroxides, alkaline earth metal hydroxides, and metal-free hydroxides, including potassium hydroxide, ammonium hydroxide, calcium hydroxide, magnesium hydroxide, ammonia, mono-, id- and tri-ethanol amines, and combinations thereof. Sodium hydroxide is preferred, and although potassium hydroxide can be employed, it is not preferred. The organic or inorganic base is preferably employed in at least an equimolar amount relative to the number of moles of polycarboxylated alcohol alkoxylated used. The polycarboxylated alcohol may also contain a polycarboxylic acid, for example, polyacrylic acid, along with the starting alcohol alkoxylate and esters of the alkoxylate of the polycarboxylic acid.

Although individually the cationic and the amphoteric surfactants are acceptable for use in the process of the present invention, it is preferred that they be used in combination with at least one surfactant from one of the other classes. Illustrative cationics include alkyl triammonium halide, non-linear alkyl dimethyl halide and alkyl dimethyl benzyl ammonium halide-containing surfactants. Illustrative amphoteric surfactants include polyglycol ether derivatives, ethoxylate oxazolin derivatives, lauramidopropyl betain and lecithin.

Suitable blends can be employed in the process of the present invention based on various combinations of the above-described surfactants. Such a blend can be any combination of two or more surfactants, between or within the above-described four broad classes of surfactants. Combinations can include blends of: anionic with anionic, anionic with nonionic, anionic with cationic, anionic with amphoteric, cationic with cationic, cationic with amphoteric, nonionic with nonionic, nonionic with amphoteric, and amphoteric with amphoteric. Likewise, ternary and quaternary blends of surfactants by selecting three or four surfactants, respectively, from within or among the above-described classes.

Suitably, any single or combination of two, three or four surfactants from the following illustrative list are suitably employed: (a) nonionics, including alkoxylated linear alcohols (such as POLY-TERGENT SLF-18 surfactant, a product of Olin Corporation), linear alcohol ethoxylates (such as NEODOL 91-8 surfactant, a product of the Shell Corporation), ethoxylated linear alkyl benzene (such as TRITON X-100 surfactant, a product of Union Carbide Corporation), and EO/PO block copolymers (such as POLY-TERGENT E-17A surfactant, a product of Olin Corporation); (b) anionics, including alkyl diphenyl ether disulfonates (such as POLY-TERGENT 2A1 surfactant, a product of Olin Corporation), alkyl phenyl ethoxylated phosphate esters (such as Wayfos M-60 surfactant, a product of Olin Corporation), carboxylated linear alcohol alkoxylates (such as POLY-TERGENT CS-1 surfactant, a product of Olin Corporation), linear alkyl benzene sulfonic acid (such as BIOSOFT S-130 surfactant, a product of Stepan Company), alpha-olefin sulfonates (such as BIO TERG AS-40 surfactant, a product of Stepan Company), dialkylsulfosuccinates (such as AROWET SC-75 surfactant, a product of Arol Chemical Products), and alkyl sulfates (such as STEPANOL SLS surfactant, a product of Stepan Company); (c) cationics including alkyl triammonium halides (such as CTAB surfactant, a product of VWR Scientific Inc.), polyoxyethylene cocoamine (such as MAZEEN surfactant, a product of PPG Industries), primary alkyl amines (such as ARMEEN surfactant, a product of Akzo Chemical Co.), dicoco dimethyl ammonium halide (such as JET QUAT surfactant, a product of Jetco Chemical Inc.), di-isodecyl dimethyl ammonium halides (such as AMMONYX K9 surfactant, a product of Stepan Company), and diethyl aminoethyl stearate (such as CERASYNT 303 surfactant, a product of ISP Van Dyke); and, (d) amphoterics, including polyglycol ether derivatives (such as ALBEGAL A surfactant, a product of Ciba-Geigy), ethoxylated oxazolin derivatives (such as ALKATERG T-IV surfactant, a product of Angus Chemicals), lauramide propyl betain (such as LEXAINE C surfactant, a product of Inolex Chemicals), lecithin (such as CANASPERSE surfactant, a product of Can Amoral), disocium cocoamphodiacetate (such as MONATERICS surfactant, a product of Mona Industries), complex fatty amine salt (such as MAFO 13 surfactant, a product of PPG Industries), and cocoamine oxide (such as ACKAMINE CO surfactant, a product of the Mcintyre Group Ltd.).

The surfactant(s) is preferably employed in a total amount of between about 0.05 and about 10%, more preferably between about 0.1 and about 5, most preferably between about 0.5 and about 1.5% by weight, based upon the weight of the aqueous or organic solution of pyrithione salt employed.

The use of the surfactants in accordance with the process of the present invention provides a variety of advantages over trying to process gelled copper pyrithione, including easy processing, including drying and filtering, of the copper pyrithione, as well as shorter cycle times due to a shorter drying time and faster dewatering of the copper pyrithione than is possible in the absence of surfactant(s). In addition, it has been found that the milling of the product copper pyrithione is facilitated by the fact that a softer copper pyrithione product is obtained in the presence of the surfactant(s).

The reaction in accordance with the process of the present invention is suitably employed to provide the desired gel-free copper pyrithione. Suitable reaction times range from about one hour or less, up to about six hours or more. The reaction temperature is suitably between about 0° and about 100° Centigrade, preferably between about 25° and about 90° Centigrade, most preferably between about 65° and about 70° Centigrade. Suitable pHs for the reaction are between 1 and 12, preferably between about 3 and about 8, most preferably between about 4 and about 5.

The following examples are intended to illustrate, but in no way limit the scope of, the present invention.

EXAMPLE 1

Preparation of Copper Pyrithione

A preferred process for carrying out the present invention entails the steps of: (1) charging alkali 2-mercapto-N-oxide solution into a reactor, (2) add the surfactant or blend of surfactants to the reactor, and (3) heat the reactor to an desired elevated temperature, and then slowly add the copper salt solution to the pyrithione/surfactant mixture in the reactor.

As an illustrative example, two hundred and forty grams of aqueous sodium 2-mercaptopyridine N-oxide (having a dry solids assay of 1.7.3 percent—also referred to herein as "sodium pyrithione") solution is charged into a 500 ml 4-neck, round-bottom flask reactor. A three-surfactant blend was prepared by mixing 25 grams of POLY-TERGENT 2A-1L anionic surfactant, 50 grams of POLY-TERGENT SLF-18 nonionic surfactant, and 37.5 grams of nonionic TRITON X-100 nonionic surfactant (all three surfactants being commercially available surfactants utilized "as received"). Two grams of the surfactant mixture was added to the flask with ongoing agitation for 20 minutes to insure proper mixing of the surfactant blend with the sodium pyrithione solution in the reactor. The reactor was then heated up to 70 degrees Centigrade over a period of between 40 and 60 minutes. A thermometer and pH probe were then inserted into the reactor, and a copper chloride-containing feed hose was connected to the reactor. The copper chloride (a 20% aqueous solution comprising 24.4 grams of solid copper chloride dihydrate) was slowly added to the heated reactor at an addition rate of 2 ml/minute. The reaction mixture was continuously stirred, the pH of the mixture was monitored until the pH reached about 4, and the sodium pyrithione in the flask was assayed until it reached 0.0% indicating that the reaction was complete. A constant temperature of 70 degrees Centigrade was maintained throughout the reaction.

Once the reaction was complete, stirring was continued for 30 minutes, and the product mixture was allowed to cool to a temperature of about 50 degrees Centigrade by standing in the lab. The resulting copper pyrithione product had a viscosity of 150 to 250 centipoise, and was easily filtered. Filtration was completed in less than 30 seconds. The resulting copper pyrithione cake was washed with cold water until the filtrate is free of ions and measures less than 1000 in a conductivity measurement. The cake was weighed and dried in an oven at 70 degrees Centigrade. About 40 to 44 grams of copper pyrithione was produced which is equivalent to almost 100% of theoretical with a copper pyrithione purity of above 98%.

The shape of dried particles of pyrithione was examined under a microscope and found to be of a needle shape, and the mass of dried needles was found to have a relatively narrow particle size distribution. By varying the types of surfactants employed, it was found that non-needle "platelets" are produced having a more symmetrical crystalline shape. The platelets are expected to be an advantageous form for use in products such as paints and personal care products (e.g., soaps, shampoos and skin care medicaments) due to the increased surface area associated with platelets, affording enhanced biocidal protection relative to the needle configuration. The platelets are also an advantageous configuration for copper pyrithione since such particles tend to provide favorable bulk density, dispersibility and/or ease of milling for subsequent processing prior to use. Advantageously the platelets will have a mean sphericity of less than about 0.65 and a median equivalent spherical diameter based on volume of at least about 2 microns but less than 15 microns.

As a comparison, when an identical procedure was conducted in the absence of surfactant, a visually gelatinous copper pyrithione product was produced that was difficult to filter, difficult to dry and difficult to handle due to its high viscosity.

What is claimed is:

1. A process for producing a solution or dispersion of gel-free copper pyrithione which comprises reacting at a reaction temperature of between about 65 degrees and about 70 degrees Centigrade, in an ion-exchange reaction, a reaction mixture comprising a copper salt, a pyrithione salt, and a carrier, to produce said solution or dispersion, having a pH of between about 4 and about 5, said reaction being carried out in the presence of a stabilizing effective amount of at least one surfactant, the total amount of said surfactant being sufficient to prevent or inhibit the formation of gels in said carrier, wherein said surfactant comprises a combination of an anionic surfactant and a nonionic surfactant.

2. The process of claim 1 wherein said anionic surfactant is selected from the group consisting of alkyl diphenylether disulfonates and wherein said nonionic surfactant is selected from the group consisting of alcohol alkoxylates.

3. The process of claim 1 wherein the total amount of said surfactant(s) is between about 0.05 and about 10% based upon the weight of the aqueous or organic solution or dispersion of pyrithione salt employed.

4. A gel-free copper pyrithione dispersion or solution produced by a process which comprises reacting at a reaction temperature of between about 65 degrees and about 70 degrees Centigrade, in an ion-exchange reaction, a reaction mixture comprising a copper salt, a pyrithione salt, and a carrier, to produce said solution or dispersion, having a pH of between about 4 and about 5, said reaction being carried out in the presence of a stabilizing effective amount of at least one surfactant, the total amount of said surfactant being sufficient to prevent or inhibit the formation of gels in said carrier, wherein said surfactant comprises a combination of an anionic surfactant and a nonionic surfactant.

5. The dispersion or solution of claim 4 wherein said anionic surfactant is selected from the group consisting of alkyl diphenylether disulfonates and wherein said nonionic surfactant is selected from the group consisting of alcohol alkoxylates.

6. The dispersion or solution of claim 4 wherein the total amount of said surfactant(s) is between about 0.05 and about 10% based upon the weight of the aqueous or organic solution or dispersion of pyrithione salt employed.

* * * * *